United States Patent [19]

Yocca et al.

[11] Patent Number: 5,278,164
[45] Date of Patent: Jan. 11, 1994

[54] TREATMENT OF ANXIETY IN BENZODIAZEPINE-WITHDRAWN PATIENTS

[75] Inventors: Frank D. Yocca, Madison; Herbert L. Smith, New Haven, both of Conn.

[73] Assignee: Bristol-Myers Squibb Co., New York, N.Y.

[21] Appl. No.: 69,654

[22] Filed: Jun. 1, 1993

Related U.S. Application Data

[63] Continuation of Ser. No. 782,010, Oct. 24, 1991, abandoned.

[51] Int. Cl.⁵ ............................................ A61K 31/495
[52] U.S. Cl. ...................................... 514/252; 514/255
[58] Field of Search .............................. 514/252, 255

[56] References Cited

U.S. PATENT DOCUMENTS 4,605,655  8/1986  Yevich et al. ................. 514/252
5,055,470 10/1991  Boissard et al. .............. 514/252

OTHER PUBLICATIONS

McMillen, et al.; N-Alkyl-Substituted Aryl-Piperazine Drugs: Relationship Between Affinity for Serotonin Receptors and Inhibition of Agression; 12(1) 53-62 (1988) (2/31).

McMillen, et al.; Reversal of neuroleptic-induced catalepsy by novel aryl-piperazine anxiolytic drugs; 40:885-887 (1988) (3/1).

Schweizer, et al.; Failure of Buspirone to Manage Benzodiazepine Withdrawal, 143:12, 1590-1592 (1986) (3/14).

Goudie, et al.; Evaluation of the Dependence potential of the selective 5-H1A agonist ipsapirone in rats and of its effects on benzodiazepine withdrawal 103:529-537 (1991) (3/20).

Costall, et al.; The Effects of Ondansetron (GR38032F) in Rats and Mice Treated Subchronically with Diazepam; 34: 769-778 (1989) (3/28).

McMillen et al., Soc. Neurosci. Abstr. vol. 13, No. 1, (1987) p. 452.

Vandermaelen, et al., European Journal of Pharmacology vol. 179, No. 3, (1990) 357-366.

File, et al., Psychopharmacology, vol. 105, No. 4, (12/91) 578-582.

Primary Examiner—Frederick E. Waddell
Assistant Examiner—K. Weddington
Attorney, Agent, or Firm—Richard P. Ryan

[57] ABSTRACT

A method of treatment of anxiety in benzodiazepine-withdrawn patients by administering BMY 14802 or, preferably, the R-(+)- enantiomer to a patient in need of such treatment.

4 Claims, No Drawings

TREATMENT OF ANXIETY IN BENZODIAZEPINE-WITHDRAWN PATIENTS

This application is a continuation of application Ser. No. 07/782,010, filed Oct. 24, 1991, now abandoned.

FIELD OF THE INVENTION

This invention is concerned with a drug bio-affecting body-treating process which employs the piperazinyl butyrophenone compound 4-[4-(5-fluoro-2-pyrimidinyl)-1-piperazinyl]-1-(4-fluorophenyl)butanol or a pharmaceutically acceptable acid addition salt thereof.

BACKGROUND OF THE INVENTION

The arylpiperazinyl butyrophenone derivative with which the present inventive method is concerned has been referred to in the prior art as BMY 14802 and also MJ 14802. The synthesis of the compound and a disclosure of its antipsychotic properties are described by Yevich, et al., in U.S. Pat. No. 4,605,655.

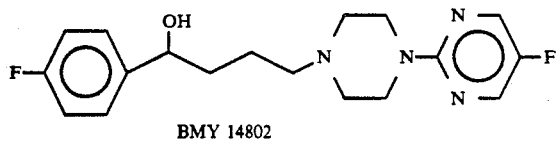

BMY 14802

Boissard, et al., have disclosed the use of BMY 14802 for treating various disorders resulting from brain ischemia in U.S. Pat. No. 5,055,470.

McMillen, et al., have studied various antipsychotic drugs, including BMY 14802, in animal models of aggression and suggest that a relationship exists between antiaggressive activity and a potential for anxiolytic effects; e.g. see *Drug Rev. Res.*, 12(1), 53–62 (1988). McMillen, et al., also disclosed in *J. Pharm. Pharmacol.*, 40: 885–887 (1988); that BMY 14802 demonstrated activity in reversing neuroleptic-induced catalepsy in a study involving members of the azapirone class of novel arylpiperazines such as the clinical anxiolytic agents buspirone, gepirone and ipsapirone. McMillen suggested that the anti-catalepsy activity correlates with the arylpiperazine's having anti-aggression action.

The archetypical arylpiperazine anxiolytic drug is buspirone. Clinical studies with buspirone however, indicate that its anxiolytic efficacy is diminished in patients being withdrawn from benzodiazepine treatment. [Schweizer, et al., *Am. J. Psychiatry*, 143: 12, 1590–1592 (1986).] Buspirone, and BMY 14802 alike, have no clinically significant benzodiazepine receptor activity. Similar conclusions were reached for a related azapirone arylpiperazine anxiolytic, ipsapirone on the basis of animal studies [Goudie, et al., *Psychopharmacology*, 103: 529–537 (1991).] Against this background, antianxiety effects of BMY 14802 would not be expected in benzodiazepine-withdrawn patients.

Due to wide usage of the benzodiazepine class of anxiolytics, in spite of their acknowledged liabilities, there exists a need for agents that are effective in treating the anxiety experienced by patients during benzodiazepine withdrawal. Costall, et al., [*Pharmacol. Biochem. Behav.*, 34: 769–778 (1989)] reported that the non-arylpiperazine anxiolytic agent ondansetron

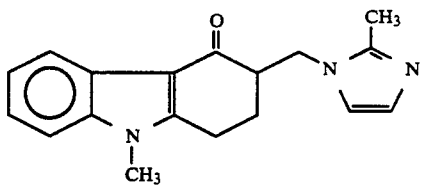

Ondansetron demonstrated anxiolytic action in an animal model of anxiety following benzodiazepine withdrawal.

No suggestion exists in this background art that would make obvious in any way the existence of a therapeutic advantage of the arylpiperazinyl antipsychotic agent BMY 14802 over recognized arylpiperazine anxiolytics for treatment of a population being withdrawn from benzodiazepine exposure.

SUMMARY OF THE INVENTION

The method of the present invention is intended to provide relief of anxiety in patients who are being withdrawn from benzodiazepine medication. The present method is effective in suppression of anxiety whether from underlying generalized anxiety disorder or triggered or exacerbated by the withdrawal process from benzodiazepine compounds. The inventive method essentially involves administration of BMY 14802, 4-[4-(5-fluoro-2-pyrimidinyl)-1-piperazinyl]-1-(4-fluorophenyl)butanol, or a pharmaceutically acceptable salt and/or hydrate thereof, to a mammal in need of such treatment. In the subject method, the (+)- enantiomeric form of BMY 14802 is preferred.

DETAILED DESCRIPTION OF THE INVENTION

Benzodiazepines have been prescribed widely over the past 25 years as effective medicaments for the treatment of anxiety. In recent years, however, there has emerged a clear recognition of liabilities associated with benzodiazepine administration. Chief among these are the development of dependence and a drug-withdrawal syndrome when their administration is halted. In this drug-withdrawn patient population, a variety of symptoms indicative of anxiety emerges. These anxiety symptoms comprise psychologic symptoms such as tension, restlessness, foreboding, irritability, anger and hostility; as well as certain somatic symptoms such as headache, sweating, tremor and insomnia. The severity and time course of these conditions vary according to the individual patient, the specific benzodiazepine being given, the severity of the underlying anxiety disorder and other treatment variables familiar to those skilled in the treatment of anxiety.

Due to the abuse and physical dependence often experienced with the benzodiazepines, other classes of anxiolytic drugs are being increasingly selected for the treatment of patients suffering from anxiety disorders. However, given the widespread exposure of anxious patients to benzodiazepines, replacement anxiolytic agents which are effective in patients who have previously experienced prolonged benzodiazepine treatment are sought. Many of the currently available anxiolytic agents, as well as new candidates in clinical development, do not appear to be effective in these benzodiazepine-withdrawn patients.

The present invention results from the discovery that BMY 14802 exhibits significant anxiolytic effects in animal tests which measure anxiety indicators in benzodiazepine-withdrawn test populations. Using a social interaction test in rats that are undergoing benzodiazepine withdrawal, BMY 14802 demonstrated significant anxiolytic effects. In contrast, buspirone did not elicit an anxiolytic response under the same conditions. Similar results were obtained from an anxiolytic test model in mice which utilizes a black and white test box for observation of exploratory behavior in test animals. [This method is described in Costall, et al., *Pharmacol. Biochem. Behav.*, 32: 777–785 (1989).]

In a test model of precipitated withdrawal in rats anxiogenesis is caused by flumazenil, a benzodiazepine antagonist, when given to rats chronically dosed with benzodiazepine. Administration of BMY 14802 resulted in a marked increase in social interaction behavior in this precipitated withdrawal model. These results indicate the useful anxiolytic effect of BMY 14802 in a population undergoing benzodiazepine withdrawal.

The present method of treatment invention essentially involves administration of BMY 14802 or a pharmaceutically acceptable salt and/or hydrate thereof, to a mammal suffering from anxiety. The novel aspect of the treatment lies in its applicability to individuals having had prior exposure to benzodiazepine therapy, particularly when the benzodiazepine administration was long term.

Since BMY 14802 has a chiral center it exists in enantiomeric forms. For use in the instant method of treatment, BMY 14802 may be administered as a racemic modification or, preferably, as the (+)-(R)-enantiomer. Pharmacologic testing in the rodent models described supra demonstrated the superiority of (+)-(R)- BMY 14802 in treating anxiety in a diazepam (+)-(R)- BMY 14802 in treating anxiety in a diazepam withdrawn test population. Also preferred is the use of the hydrochloride salt of BMY 14802 in the inventive method.

Although the dosage and dosage regimen of BMY 14802 must in each case be carefully adjusted, utilizing sound professional judgment and considering the age, weight and condition of the recipient, the route of administration and the nature and extent of anxiety, generally, the daily dose will be from about 0.05 g to about 5 g, preferably 0.3 g to 3 g, when given orally. In some instances, a sufficient therapeutic effect can be obtained at lower doses while in others, larger doses will be required. As is apparent to one skilled in clinical pharmacology, the amount of BMY 14802 comprising the daily dose may be given in a single or divided dose, taking into account those principles understood by the skilled practitioner and necessary for his practice of the art.

The term "systemic administration" as used herein refers to oral, sublingual, buccal, transnasal, transdermal, rectal, intramuscular, intravenous, intraventricular, intrathecal, and subcutaneous routes. Generally, it will be found that when a compound of the present invention is administered orally a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective anxiolytic amount of BMY 14802 or a pharmaceutically acceptable acid addition salt and/or hydrate thereof and a pharmaceutically acceptable carrier. Pharmaceutical compositions for effecting such treatment will contain a major or minor amount (e.g. form 95% to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a predetermined amount of the drug corresponding to a fraction or multiple of the dose which is calculated to produce the desired therapeutic response. In usual practice, the dosage units contain 1, $\frac{1}{2}$, $\frac{1}{3}$, or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three, or more times a day. It is envisioned that other therapeutic agents can also be present in such a composition. Pharmaceutical compositions which provide from 0.01 to 1 g of the active ingredient per unit dose are preferred and are conventionally prepared as tablets, lozenges, capsules, powders, aqueous or oily suspensions,syrups, elixirs, and aqueous solutions. Preferred oral compositions are in the form of tablets, capsules, and may contain conventional excipients such as binding agents. (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g., magnesium stearate, talc, polyethylene glycol or silica), disintergrants (e.g. starch) and wetting agents (e.g. sodium lauryl sulfate). Solutions or suspensions of BMY 14802 with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of BMY 14802 or one of its salt forms in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

When transnasal application is intended, the BMY 14802 pharmaceutical composition is formulated in a pharmaceutical composition which enhances penetration of the nasal mucosa. Such formulations normally employ fatty acid salts of the BMY 14802 base compound and their preparation and use would be known to one skilled in the pharmaceutical arts.

DESCRIPTION OF SPECIFIC EMBODIMENTS

BMY 14802 in the form of the hydrochloride salt was employed in the procedures of the following examples.

Example 1

Social Interaction Test - Benzodiazepine Withdrawal

In this model, rats are dosed twice daily for 7 days with 10 mg/kg diazepam. After cessation of diazepam treatment, rats are given test anxiolytic agents at various time points (8, 24, 48 and 96 hour) during a resulting benzodiazepine-withdrawal period.

Eight pairs/group of animals are used, each pair receiving the same drug is placed in a plexiglass area equipped with photoelectric beams for recordation of locomotor activity. Each pair is observed for five-minute periods for socially-interactive behaviors (i.e. sniffing and grooming, genital investigation, following, walking around and crawling over or under the other animal). Time spent exhibiting these behaviors is recorded in seconds. Drugs which result in a significant increase in social interaction time between the test animals are considered to be effective anxiolytics appropriate for benzodiazepine withdrawn subjects. The interruption of infrared photobeams provides a measure of general locomotor activity for each drug tested. Social interaction time is analyzed by student's t-test for $p \leq 0.05$ significance.

Example 2

Exploration of Mice in a Black and White Test Box Model of Anxiety

This paradigm (cf: Costall, et al., (1989) *Pharmacology Biochemistry & Behavior*, Vol 32, pp 777-785) utilizes the natural aversion of rodents to open fields as a component of their exploratory behavior. After a period of adaptation in the darkened testing room, drug-treated mice are placed in a metal test box divided into a dark area painted black and a brightly illuminated white area. These two compartments are connected by an opening in the partition. After placing mice in the bright chamber the operator withdraws and the behavior of the mice in the test box is observed by remote video recording and certain behaviors are noted:

1. exploratory rearings in each chamber,
2. crossings between chambers,
3. movement within each chamber,
4. time spent in each chamber, and
5. latency of initial movement from the bright into the dark chamber.

Compounds which exhibit an anxiolytic profile of action cause mice to increase exploratory activity and time spent in the bright chamber with a decrease in the dark chamber. An opposite pattern of behavior is seen in mice treated with an anxiogenic agent, e.g. FG 7142, which induces anxiogenic action clinically.

Example 3

Precipitated Withdrawal Model

Harlan Sprague Dawley male rats, weights between 200-350 g housed in groups of 5 animals per cage, were dosed twice daily for 7 days with 10 mg/kg, IP (intraperitoneally) of diazepam. After the first dose on the 7th day cessation of diazepam treatment began. The benzodiazepine withdrawal period was tested at various time points (8, 24, 48 and 96 hours) post diazepam administration. The test drug, benzodiazepine antagonist, flumazenil (RO 15 1788) was administered 30 min prior to testing at 10.0 mg/kg, IP for precipitation of a withdrawal response. The result was a decrease (anxiogenic response) in the amount of time spent exhibiting social interaction below controls at 8 and 24 hours post diazepam withdrawal.

BMY 14802 was tested in animals precipitated for anxiogenesis at a dose of 0.1 mg/kg, IP. Flumazenil was administered at 10.0 mg/kg, IP 60 min prior to testing followed by 30 min pretreatment with BMY 14802. BMY 14802 significantly increased social interaction behavior to levels above those seen with animals pretreated with flumazenil or vehicle alone. This increase was observed for all times tested.

Example 4

(R)-(+)-BMY 14802

The preparation of racemic BMY 14802 and its resolution into the enantiomers is fully described in U.S. Pat. No. 4,605,655.

Essentially the racemic BMY 14802 in base form is treated with a commercially available isocyanate resolving agent such as (S)-(−)- or (R)-(+)- or methylbenzyl isocyanate to provide a diastereomeric carbamate mixture that is separated into the diastereomers which are then cleaved with trichlorosilone to provide the (+)-R- and (−)-S-enantiomers of BMY 14802.

In practice, use of the (R)-(+)- isocyanate gives a mixture in which the crystalline material is the diastereomer of (R)-(+)- BMY 14802. Separation by simple filtration, followed by cleavage yields the pure (R)-(+)-enantiomer of BMY 14802.

We claim:

1. A method of treating anxiety in patients that have been withdrawn from benzodiazepine medication, the method comprising administration to these patients suffering from anxiety of an effective anxiolytic dose of BMY 14802, chemically 4-[4-(5-fluoro-2-pyrimidinly)-1-piperazinyl]-1-(4- fluorophenyl) butanol, or a pharmaceutically acceptable acid addition salt and/or hydrate thereof.

2. The method of claim 1 wherein the pharmaceutically acceptable addition salt of BMY 14802 is the hydrochloride salt.

3. The method of claim 1 wherein the administration of BMY 14802 is by the oral route of administration.

4. The method of claim 1 comprising administration of a pharmaceutical composition comprising BMY 14802 or a pharmaceutically acceptable salt and/or hydrate thereof in a pharmaceutically acceptable carrier therefor.

* * * * *